(12) United States Patent
Stamp et al.

(10) Patent No.: US 11,272,943 B2
(45) Date of Patent: Mar. 15, 2022

(54) BONE STAPLE DRILL GUIDE WITH DRILL CARTRIDGE AND COMPRESSION DEVICE

(71) Applicant: ORTHO SOLUTIONS HOLDINGS LIMITED, Littleton, CO (US)

(72) Inventors: Kevin Stamp, Sheffield (GB); Alister Maclure, Chelmsford (GB); Dustin Ducharme, Littleton, CO (US)

(73) Assignee: ORTHO SOLUTIONS HOLDINGS LIMITED, Littleton, CO (US)

( * ) Notice: Subject to any disclaimer, the term of this patent is extended or adjusted under 35 U.S.C. 154(b) by 0 days.

(21) Appl. No.: 16/996,107

(22) Filed: Aug. 18, 2020

(65) Prior Publication Data
US 2021/0052289 A1    Feb. 25, 2021

Related U.S. Application Data

(60) Provisional application No. 62/888,759, filed on Aug. 19, 2019.

(51) Int. Cl.
| | |
|---|---|
| *A61B 17/56* | (2006.01) |
| *A61B 17/58* | (2006.01) |
| *A61B 17/064* | (2006.01) |
| *A61B 17/84* | (2006.01) |
| *A61F 2/30* | (2006.01) |
| *A61B 17/17* | (2006.01) |
| *A61B 17/00* | (2006.01) |
| *A61B 17/68* | (2006.01) |

(52) U.S. Cl.
CPC .......... *A61B 17/17* (2013.01); *A61B 17/0642* (2013.01); *A61B 17/848* (2013.01); *A61B 17/1775* (2016.11); *A61B 17/1782* (2016.11); *A61B 2017/00526* (2013.01); *A61B 2017/00867* (2013.01); *A61B 2017/681* (2013.01)

(58) Field of Classification Search
CPC combination set(s) only.
See application file for complete search history.

(56) References Cited

U.S. PATENT DOCUMENTS

2017/0209192 A1* 7/2017 Krauss ............... A61B 17/8866

* cited by examiner

*Primary Examiner* — Sameh R Boles
(74) *Attorney, Agent, or Firm* — Hudak, Shunk & Farine Co. LPA

(57) ABSTRACT

The invention is a drill guide assembly for a superelastic bone staple having a bridge member and opposing open legs and the drill guide assembly has a pair of legs that can be moved toward or away from each other and accepts a drill guide cartridge for the holes for the staple legs.

14 Claims, 2 Drawing Sheets

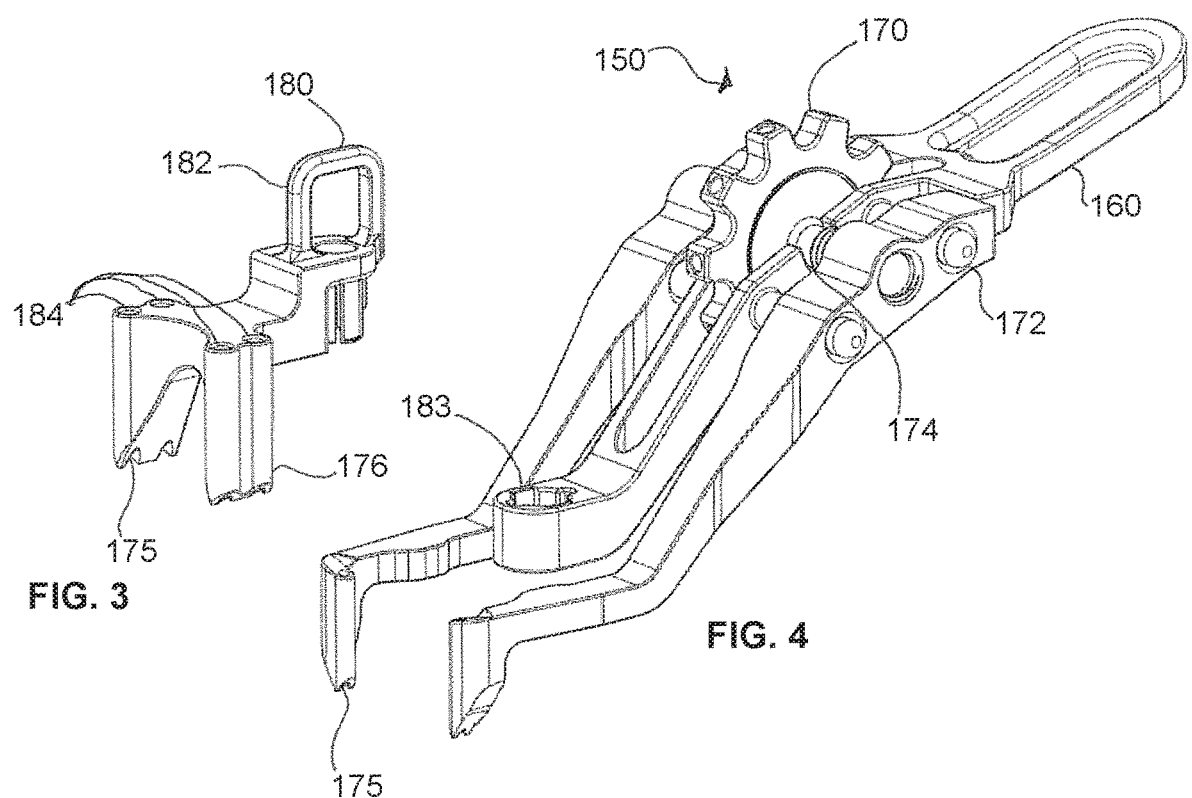

BONE STAPLE DRILL GUIDE WITH DRILL CARTRIDGE AND COMPRESSION DEVICE

FIELD OF THE INVENTION

The invention relates to a drill guide assembly for use assembly for use with a room temperature superelastic U-shaped Nitinol staple used for bone fixation, which has a compression or distraction aspect, and which accepts a cartridge for the staple leg drill guide so as to allow the drill guide to be used with various configuration and size staples.

BACKGROUND OF THE INVENTION

Over 1.8 million orthopedic trauma fixation procedures were performed in the US in 2016, and the market is expected to reach over $4 billion by 2025. The fastest growing part of the market is the staple fixation segment, which is also expected to remain the fastest growing through to 2025. The primary drivers for growth are reportedly a reduced operating time as compared to screws, and plates.

While the state of the art has advanced the use of bone staples, there remain issues in the use and design of the instruments designed for the surgical implantation of surgical procedures while taking inventory concerns into consideration. Thus, the invention relates to a drill guide that can be used for a variety of staple models, and which doubles as a tool to affect compression between bone segments to help induce fusion when the staple is deployed.

SUMMARY OF THE INVENTION

The invention provides a drill guide assembly for a superelastic compressive bone staple. The staple has a bridge member that extends a length along an axis and which joins two or more legs spaced apart along the axis and is fabricated in a closed (converging legs) shape and is mechanically deformed or "activated" by the inserter during use to induce the superelastic shape memory properties. This allows the staple to compress bone segments. The drill guide assembly includes a compressor/distractor that has a lateral movement mechanism that spreads apart or contracts the flange ends of the drill guide which are supported by k-wires toward each other and makes room for the staple drill guide cartridge that is captured in an appropriate keyed recess in the drill guide body.

The staple of the present invention is configured to accommodate fixation procedures in the forefoot, midfoot, rearfoot and hand, and the inserter (which can be disposable) allows implantation of the staple in bone in a surgical procedure so as to apply a compressive force across a division of bone segments. A preferable configuration for the bone staple is a substantially U-shaped staple, i.e. a staple having a transverse bridge member and downwardly extending legs (one or more pairs), which can be biased into a parallel "activated position" for insertion into the bone, and then released into a compressive configuration.

The invention also relates to a drill guide/compression device that includes a laterally opposed pair of k-wire channels and a mechanism that compresses or expands the set of k-wire tips laterally. The drill guide body further has a complex opening that forms a clip to secure a drill cartridge in the opening so that various pilot holes can be drilled using a single drill guide body.

BRIEF DESCRIPTION OF THE DRAWINGS

FIG. 2 is a compression insert for use in a second embodiment of the invention;

FIG. 3 is a drill guide cartridge for use with the drill guide assembly of FIG. 2; and FIG. 4 is a drill guide/distractor body of the drill guide assembly of FIG. 2.

DETAILED DESCRIPTION OF THE INVENTION

Figure 1:
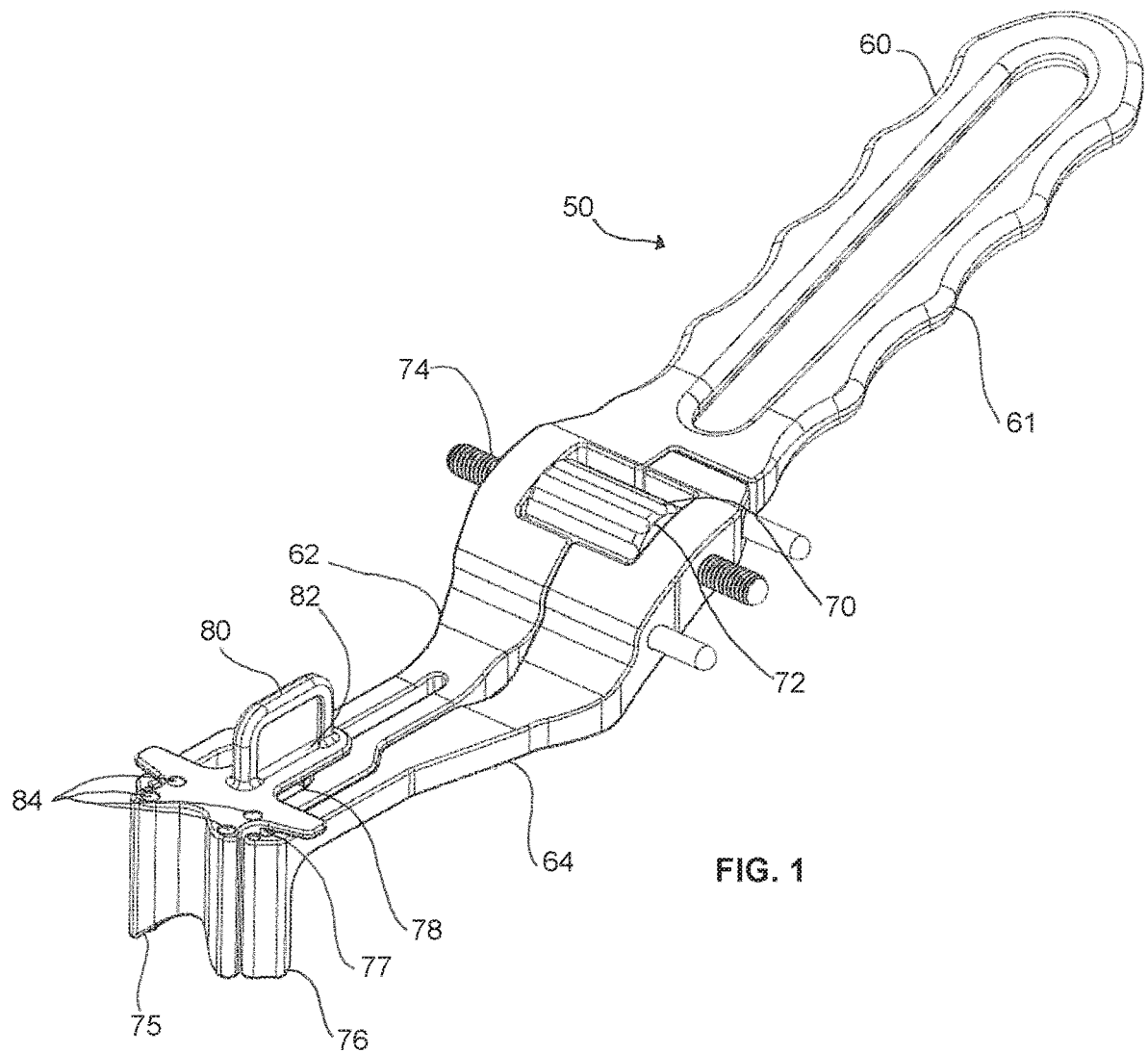
FIG. 1 shows a top side perspective of a drill guide in accordance with the invention.

The present invention comprises a drill guide assembly 50 for use with a room temperature superelastic Nitinol compression staple 10 for bone fixation in the surgical management of fractures and reconstruction of the foot and hand. Typically, the staples used with the present invention have a nominally U-shaped profile with a bridge member 14 spanning a space between opposing legs 12 (and it should be understood that the present inserter is also suitable for use with a staple having four legs in which each end of the bridge member includes a pair of legs, or alternatively, the staple could have three legs with a pair on one end, and a single leg opposing the pair). The drill guide assembly 50 of the invention is illustrated herein for use with a staple having two opposing pairs of legs that are joined by a bridge member of the staple, but it should be understood that the staple has two or more, and preferably 2, 3, or 4 transversely extending legs 1 that will engage bones or bone segments through the cortical surfaces. The legs are spaced apart from each other and joined together by bridge member that extends across the area between legs at either end of the bridge member. For the purpose of deployment, the legs extend downward parallel to each other and advantageously transverse to the bridge member. The staple is comprised of a material is elastic and has the ability to recover an original un-deformed shape so as to apply a compressive force. An example of a suitable material is a superelastic material which is activated into the superelastic state by mechanical deformation.

The staple of the present invention is configured to accommodate fixation procedures in the forefoot, midfoot, rearfoot and hand, and the inserter (which can be disposable) allows implantation of the staple in bone in a surgical procedure so as to apply a compressive force across a division of bone segments. A preferable configuration for the bone staple is a substantially U-shaped staple, i.e. a staple having a transverse bridge member and downwardly extending legs (one or more pairs), which can be biased into a parallel "activated position" for insertion into the bone, and then released into a compressive configuration.

The drill guide/compression instrument 50 of the present invention comprises an assembly of a drill guide cartridge 80 and a handle member 60 having an elongated handle 61 which is shaped having scalloped edges to accommodate being grasped while a compression/tension mechanism 70 includes a turn member 72 on a transverse screw 74. The handle member 60 extends into a first drill guide leg member 62 that remains stationary relative to the handle 61 and a second drill guide leg member 64 that opens and closes across a lateral gap by means of the distraction mechanism. More precisely, the user can open and close the gap between the legs by turning the turn member 72 which moves on the transverse screw 74 to drive the second leg closer to or farther away from the first leg. Each of the first and the second leg include a transversely extending extension 75, 76 which has a cannulation 77 for a k-wire. Thus, the k-wires can be driven into the bone or bone segments, and the drill guide/distractor can be used to position or apply compression to the bone or bone segments, either before or after the drill guide is used to drill pilot holes for the legs of the associated bone staple.

Accordingly, one of the drill guide legs, here, the first leg, 62 includes a complex recess 78 that allows a drill guide cartridge 80 to be inserted into the drill guide/compression assembly. The drill guide cartridge includes a finger handle 82, and template member 82 that include spaced holes 84 according to various staple configurations. The drill guide cartridge also has a boss that cooperates with the complex recess to securely hold the cartridge in place relative to the handle member 60.

FIGS. 2-4 show a second embodiment of the drill guide assembly 150 which includes a handle member 160 with a compression mechanism 170 having a turn member 172 on a transverse screw 174, that operates to apply compression to the extensions 175 in a similar manner to the first embodiment. A drill guide cartridge 180 and compression cartridge 185 form part of the assembly. The cartridge 180 has a handle 182, and template member 182 including holes 184 according to various staple configurations. The cartridge and compression members 180 have a boss 187 that cooperates with the complex recess 183 to hold the cartridge in place relative to the handle member 60.

The operation of the inserter 50 for implantation of the compression staple is described as follows: After the bone segments to be fused are prepared for receiving the compression staple 10, the user places the drill guide/compression assembly on the bone segments and drives k-wires through the k-wire holes. The distraction/compression mechanism is used to apply pressure as is warranted, and the appropriate drill guide cartridge is selected so that holes can be drilled for the appropriate staple. The drill guide is removed, by drawing off the k-wires which are left in position for the purpose of marking the location of the staple. The staple is inserted by deploying the staple into the activated position and tamping it into the drilled holes.

The staple drill guide/compression assembly of the present invention is suitable for manufacture via injection molding but could also be fabricated from other manufacturing techniques such as, but not limited to, machined, 3-d printed or stamped components. The inserter can be fabricated from plastic or metal materials, or a combination of both. The staple and instruments are configured to accommodate different fixation procedures in the forefoot, midfoot, rearfoot and hand, and the inserter allows implantation of the staple in bone in a surgical procedure so as to apply a compressive force across a division of bone segments for fracture and osteotomy fixation of the hand and foot, including joint arthrodesis and to stabilize and dynamically compress bone fragments to facilitate osteosynthesis.

What is claimed is:

1. A bone staple drill guide for use with a bone staple having a set of legs and the bone staple drill guide comprising a pair of a first leg and a second leg extending along a longitudinal axis, the first leg including an extension which extends transversely to the longitudinal axis and which includes a first cannulation to form a first channel to accept a first k-wire and the second leg including an extension which extends transversely to the longitudinal axis and which includes a second cannulation to form a second channel to accept a second k-wire and the first and second cannulation thus forming a laterally opposed pair of k-wire channels being separated by a distance and a mechanism to change the distance, and the drill guide further including a set of openings to guide the drilling of openings for the set of staple legs, wherein the openings are contained in a cartridge and are spaced according to various staple configurations.

2. A bone staple drill guide as set forth in claim 1, wherein the mechanism to change the distance comprises an axle with a turn member.

3. A bone staple drill guide as set forth in claim 2, wherein the axle is a threaded member which extends transverse to the longitudinal axis between the first leg and the second leg and the turn member is a threaded thumb member that mates with the threaded member.

4. A bone staple drill guide as set forth in claim 3, wherein the cartridge has a press fit relationship with the bone staple drill guide.

5. A bone staple drill guide as set forth in claim 4, wherein the bone staple drill guide further includes a handle which extends away from the legs in the direction of the longitudinal axis.

6. The bone staple drill guide as set forth in claim 1, wherein the first leg extension and the second leg extension each include a flange end and the mechanism to change the distance a includes a compressor/distractor that has a lateral movement mechanism that spreads apart or contracts the flange ends of the drill guide toward each other and to make room for a staple drill guide cartridge.

7. The bone staple and drill guide assembly as set forth in 6, wherein the drill guide further includes a keyed recess that captures the staple drill guide cartridge.

8. A bone staple drill guide as set forth in claim 1, further comprising a bone staple that has a transverse bridge member and at least one pair of downwardly extending legs which can be biased into a parallel activated position for insertion into the bone, and then released into a compressive configuration.

9. The bone staple drill guide as set forth in claim 8, which further has a complex opening that forms a clip to secure a drill cartridge in the opening so that various pilot holes can be drilled using the device.

10. The bone staple drill guide as set forth in claim 9, wherein the drill guide further has an elongated handle which is shaped having scalloped edges to accommodate being grasped.

11. The bone staple drill guide as set forth in claim 9, wherein the drill guide further a turn member on a transverse screw.

12. The bone staple drill guide as set forth in claim 11, wherein the guide handle extends into a first drill guide leg member which includes one of the k-wire channels of the laterally opposed pair of k-wire channels and which remains stationary relative to the handle and the drill guide includes a second drill guide leg member that includes the other of the k-wire channels of the laterally opposed pair of k-wire channels and the second leg member opens and closes across a lateral gap by means of a distraction mechanism.

13. The bone staple drill guide as set forth in claim 12, wherein a user can open and close the lateral gap between the first dill guide leg member and the second drill guide leg member by turning the turn member on the transverse screw to drive the second leg member closer to or farther away from the first leg member.

14. The bone staple drill guide as set forth in claim 11, further including a compression member that can be used to apply a compression force to the bridge member of the bone staple.

* * * * *